(12) United States Patent
Nieskens et al.

(10) Patent No.: US 10,633,301 B2
(45) Date of Patent: Apr. 28, 2020

(54) METHOD FOR STABLE OPERATION OF MICROPOROUS STRUCTURES IN AN OXYGENATE CONVERSION PROCESS

(71) Applicant: Dow Global Technologies LLC, Midland, MI (US)

(72) Inventors: Davy L. S. Nieskens, Terneuzen (NL); Aysegul Ciftci Sandikci, Eindhoven (NL); Peter E. Groenendijk, Ternezeun (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/471,194

(22) PCT Filed: Dec. 14, 2017

(86) PCT No.: PCT/US2017/066263
§ 371 (c)(1),
(2) Date: Jun. 19, 2019

(87) PCT Pub. No.: WO2018/118608
PCT Pub. Date: Jun. 28, 2018

(65) Prior Publication Data
US 2020/0024213 A1   Jan. 23, 2020

Related U.S. Application Data

(60) Provisional application No. 62/437,165, filed on Dec. 21, 2016.

(51) Int. Cl.
| | | |
|---|---|---|
| *C07C 1/22* | (2006.01) | |
| *C07C 11/04* | (2006.01) | |
| *C07C 9/06* | (2006.01) | |
| *C07C 9/08* | (2006.01) | |
| *C07C 11/06* | (2006.01) | |
| *B01J 29/40* | (2006.01) | |

(52) U.S. Cl.
CPC .................. *C07C 1/22* (2013.01); *C07C 9/06* (2013.01); *C07C 9/08* (2013.01); *C07C 11/04* (2013.01); *C07C 11/06* (2013.01); *B01J 29/40* (2013.01)

(58) Field of Classification Search
CPC ........... C07C 1/20; C07C 11/02; C07C 11/06; C07C 1/0435; C07C 1/22; B01J 29/40
See application file for complete search history.

(56) References Cited

U.S. PATENT DOCUMENTS

| | | | |
|---|---|---|---|
| 4,755,536 A * | 7/1988 | Mauldin | C07C 1/20 518/709 |
| 6,534,692 B1 | 3/2003 | Barger et al. | |
| 6,872,867 B1 | 3/2005 | Senetar | |
| 8,536,396 B2 * | 9/2013 | Dath | C07C 1/22 585/638 |

FOREIGN PATENT DOCUMENTS

| | | |
|---|---|---|
| WO | 0123500 A1 | 4/2001 |
| WO | 2008110530 A1 | 9/2008 |

OTHER PUBLICATIONS

Bjorgen et al., "Methanol to Gasoline Over Zeolite H-ZSM-5: Improved Catalyst Performance by Treatment with NaOH", Applied Catalysis A: General, vol. 345, Issue 1, Jul. 31, 2008, pp. 43-50.
Lin et al., Composition extending lifetime of alcohol dehydration catalyst, IP.com Journal, 2012, Volume12, Issue7A, pp. 24.
Marchi et al., "Catalytic Conversion of Methanol to Light Alkenes on SAPO Molecular Sieves", 1991, Appl. Catal., 139.
Schulz et al., ""Coking" of Zeolites During Methanol Conversion: Basic Reactions of the MTO-MTP– and MTG Processes", Catalysis Today, 2010,183-194.
International Search Report and Written Opinion pertaining to PCT/US2017/066263, dated Mar. 14, 2018.

* cited by examiner

*Primary Examiner* — Sharon Pregler
(74) *Attorney, Agent, or Firm* — Dinsmore & Shohl LLP

(57) ABSTRACT

A process for converting oxygenates to hydrocarbons includes introducing a feed stream having at least one oxygenate into a reaction zone, and introducing a hydrogen gas stream into the reaction zone. In the reaction zone the feed stream and the hydrogen gas stream are simultaneously contacted with a catalyst, and the catalyst includes a solid microporous acid component having 8-MR to 10-MR access. The hydrogen gas stream in the reaction zone has a partial pressure from 1 bar (100 kPa) to 48 bar (4800 kPa), and the reaction zone is at a temperature from 350° C. to 500° C.

15 Claims, 1 Drawing Sheet

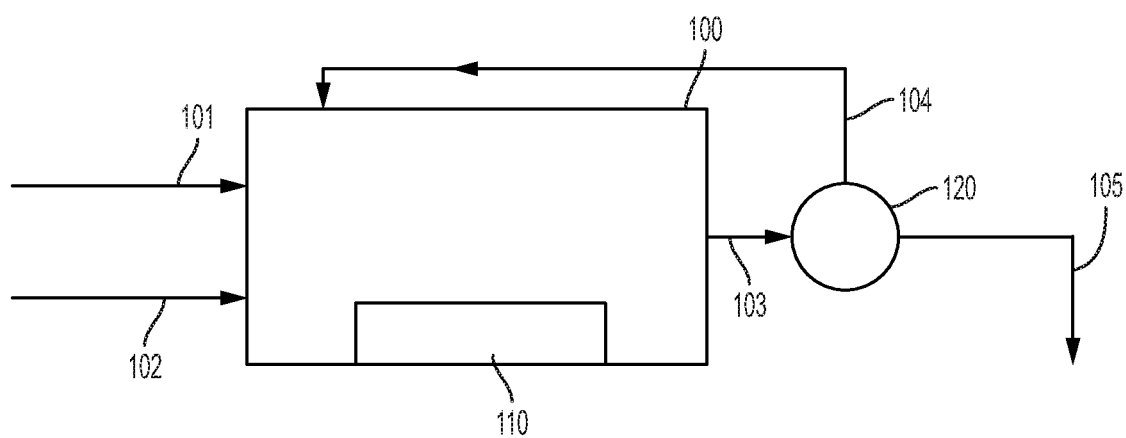

METHOD FOR STABLE OPERATION OF MICROPOROUS STRUCTURES IN AN OXYGENATE CONVERSION PROCESS

CROSS-REFERENCE TO RELATED APPLICATIONS

This application claims priority to U.S. Provisional Application Ser. No. 62/437,165 filed on Dec. 21, 2016, the entire disclosure of which is hereby incorporated by reference.

BACKGROUND

Field

The present specification generally relates to processes and systems for converting oxygenates to desired products while maximizing the lifetime and efficiency of microporous structures that are used in a catalyst package. In particular, the present specification relates to processes for converting oxygenates to hydrocarbons where a hydrogen gas stream and a feed stream comprising the oxygenates are contacted with a catalyst package comprising a solid microporous acid component.

Technical Background

Solid microporous acid components are industrially used to convert oxygenates to hydrocarbons, such as in a Methanol-To-Olefins (MTO) process, Methanol-To-Propylene (MTP) process, Methanol-To-Gasoline (MTG) process, and Hybrid Catalyst processes (e.g., the conversion of syngas to hydrocarbons via a methanol intermediate). In these processes, the oxygenate concentration in the feed and/or reactor can vary widely from relatively high—such as in a MTO-type applications—to relatively low—such as in Hybrid Catalyst-type processes. Regardless of the process that is used, the problem with using solid microporous acid components is their relatively short lifetime. During the feed to product reaction, the solid microporous acid component becomes inactivated and requires regeneration, which can involve expensive regeneration equipment, expensive regeneration processes, expensive reactors—such as fluidized bed reactors and others with continuous removal and regeneration—and a loss of production time.

Accordingly, a need exists for processes that are capable of extending the lifetime of solid microporous acid components in catalyst packages, thereby decreasing the need for costly regeneration processes and equipment.

SUMMARY

According to one embodiment, a process for converting oxygenates to hydrocarbons, comprises: introducing a feed stream comprising at least one oxygenate into a reaction zone; introducing a hydrogen gas stream into the reaction zone; contacting the feed stream and the hydrogen gas stream simultaneously with a catalyst in the reaction zone, wherein the catalyst comprises a solid microporous acid component having 8-MR to 10-MR access. The hydrogen gas stream in the reaction zone has a partial pressure from greater than or equal to 1 bar (100 kPa) to less than or equal to 48 bar (4800 kPa), and the reaction zone is at a temperature from greater than or equal to 350° C. to less than or equal to 500° C.

According to another embodiment, a process for converting oxygenates to hydrocarbons, comprises: introducing a feed stream comprising at least one oxygenate into a reaction zone; introducing a hydrogen gas stream into the reaction zone; contacting the feed stream and the hydrogen gas stream simultaneously with a catalyst in the reaction zone, wherein the catalyst comprises a solid microporous acid component having 8-MR to 10-MR access. The hydrogen gas stream in the reaction zone has a partial pressure from greater than or equal to 1 bar (100 kPa) to less than or equal to 40 bar (4000 kPa). The at least one oxygenate in the reaction zone has a partial pressure from greater than or equal to 0.01 bar (1 kPa) to less than or equal to 0.05 bar (5 kPa), and the reaction zone is at a temperature from greater than or equal to 375° C. to less than or equal to 425° C.

According to yet another embodiment, a process for converting oxygenates to hydrocarbons, comprises: introducing a feed stream comprising at least one oxygenate into a reaction zone; introducing a hydrogen gas stream into the reaction zone; contacting the feed stream and the hydrogen gas stream simultaneously with a catalyst in the reaction zone, wherein the catalyst comprises a solid microporous acid component having 8-MR to 10-MR access. The hydrogen gas stream in the reaction zone has a partial pressure from greater than or equal to 1 bar (100 kPa) to less than or equal to 48 bar (4800 kPa). The at least one oxygenate in the reaction zone has a partial pressure from greater than or equal to 0.1 bar (10 kPa) to less than or equal to 6.75 bar (675 kPa), and the reaction zone is at a temperature from greater than or equal to 425° C. to less than or equal to 475° C.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The FIGURE schematically depicts a reaction zone according to embodiments disclosed and described herein.

DETAILED DESCRIPTION

Reference will now be made in detail to embodiments of processes for converting oxygenates to hydrocarbons while stabilizing a solid microporous acid component in a catalyst package, embodiments of which are illustrated in the accompanying drawing. In one embodiment, a process for converting oxygenates to hydrocarbons, comprises: introducing a feed stream comprising at least one oxygenate into a reaction zone; introducing a hydrogen gas stream into the reaction zone; contacting the feed stream and the hydrogen gas stream simultaneously with a catalyst in the reaction zone, wherein the catalyst comprises a solid microporous acid component having 8-MR to 10-MR access, wherein the hydrogen gas stream in the reaction zone has a partial pressure from greater than or equal to 1 bar (100 kPa) to less than or equal to 48 bar (4800 kPa), and the reaction zone is at a temperature from greater than or equal to 350° C. to less than or equal to 500° C.

In conventional oxygenate conversion processes, the lifetime of a solid microporous acid component is relatively short. As used herein the lifetime of the solid microporous acid component is defined as the cumulative amount of oxygenate converted to $C_2+C_3$ hydrocarbons per gram of microporous acid component up to the point where the yield to $C_2+C_3$ hydrocarbons has dropped to zero. For instance, the lifetime of SAPO-34 in an MTO process has been reported to be up to approximately 10 gram MeOH converted into $C_2$-$C_4$ hydrocarbons per gram of SAPO-34. See e.g., Marchi, A. J. et al., 71 Appl. Catal., 139 (1991). Further, the lifetime of ZSM-5 in an MTO process is reported to be 123 gram MeOH converted into hydrocarbons per gram of ZSM-5. See e.g., Schulz et al., 154 Catalysis Today 183-194 (2010). These lifetimes of SAPO-34 and ZSM-5 are representative of lifetimes for solid microporous acid components used industrially in MTO and MTP processes. However, it is known that the lifetime of solid microporous acid in conversion of oxygenates to hydrocarbons depends on many factors, such as crystal size, acid strength and pore structure. Both SAPO-34 and ZSM-5 represent solid microporous acid with long lifetimes and many other solid microporous acids have shorter lifetimes. While the solid microporous acid components aid in efficiently producing hydrocarbons from oxygenates, the limited lifetime of the solid microporous acid components is one limitation in converting oxygenates to hydrocarbons that is addressed by embodiments of the processes disclosed herein. In particular, it was found that introducing hydrogen into the reaction zone where oxygenates are converted to hydrocarbons increases the lifetime of a solid microporous acid component in a catalyst package.

In particular, it was discovered that introducing hydrogen gas into a reaction zone at a certain pressure and a certain temperature effectively and significantly extends the lifetime of solid microporous acid components in an oxygenate-to-hydrocarbon process. Thus, embodiments include processes in which a certain amount of hydrogen is co-fed or recycled into a reaction zone in which the conversion of oxygenates to hydrocarbons takes place. The presence of hydrogen in such a reaction zone extends the lifetime of the catalyst. In some embodiments, a specific oxygenate partial pressure is matched to a specific hydrogen gas partial pressure and a specific reaction temperature so that the lifetime of the solid microporous acid component is increased, in some embodiments, to at least 450 g oxygenate converted/g solid microporous acid component. It was not previously thought that introducing hydrogen gas to the oxygenate-to-hydrocarbon conversion process would yield such a result.

Previously, hydrogen has been used in oxygenate-to-hydrocarbon conversion processes as an inert diluent that dilutes an oxygenate, such as, for example, methanol, in a feedstock and allows the oxygenate to be more efficiently converted to desirable olefin products, as opposed to less-desirable paraffin products. See U.S. Pat. Nos. 6,534,692, 6,872,867, and WO 2008/110530 A1. The conventional thought was that hydrogen was relatively inert in the reaction process and did not have an effect, either positive or negative, on the lifetime of the catalyst in oxygenate-to-hydrocarbon conversion processes. However, embodiments of the oxygenate-to-hydrocarbon conversion processes according to embodiments disclosed and described herein show that when hydrogen is present in a reaction zone where the oxygenate-to-hydrocarbon process takes place, the lifetime of a solid microporous acid component can be increased.

With reference now to the FIGURE, a reaction zone 100 comprises a catalyst 110, an inlet for a hydrogen gas stream 101, an inlet for a feed stream 102, and an outlet for a product stream 103. In addition to the reaction zone 100, a separator 120 may be used to separate hydrogen from the product stream 103 into a hydrogen recycle stream 104 and a final product stream 105.

In embodiments, the catalyst 110 comprises a solid microporous acid component, and in some embodiments, the catalyst comprises a solid microporous acid component having eight to ten membered ring (MR) access. In particular embodiments, the catalyst comprises a solid microporous acid component having 8-MR access. In such embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. In other embodiments, the catalyst comprises a solid microporous acid component having 10-MR access and having an MFI framework type corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. Examples of these may include, but are not necessarily limited to: CHA embodiments selected from SAPO-34 and SSZ-13; and AEI embodiments such as SAPO-18. As the term is used herein, "SAPO" molecular sieves are defined as silicoaluminophosphate materials having a silicon content of at least 0.01 wt %, such as at least 0.1 wt %, and at least 0.5 wt %. Many of these materials will have a silicon content of at least 5 wt % or greater. Thus, based upon this definition, molecular sieves that are primarily aluminophosphates, but actually contain very minor amounts of silicon (i.e., less than 0.01 wt %) would still be classified as "ALPO" molecular sieves. In other embodiments the molecular sieve may be ZSM-5 aluminosilicate having an MFI framework type. As the term is used herein, "ZSM-5" molecular sieves are defined as aluminosilicate materials having an aluminum content of at least 0.01 wt %, such as at least 0.1 wt %, and at least 0.5 wt %. Combinations of molecular sieves having any of the above framework types may also be employed in embodiments. It should be understood that the solid microporous acid component may have different membered ring access depending on the desired product. For instance, solid microporous acid components having 8-MR to 10-MR access could be used depending on the desired product.

As noted above, the lifetime of solid microporous acid components is relatively short. However, in processes of embodiments disclosed and described herein, hydrogen is added to the reaction zone 100 to increase the lifetime of the solid microporous acid component. Without being bound by any particular theory, it is believed that the oxygenate to hydrocarbon conversion deactivates the solid microporous acid component over time by depositing carbonaceous species on or in this microporous acid component. This degradation is primarily a function of the partial pressure of the oxygenate, such as, for example, methanol, at the active site of the catalyst (i.e., the microporous acid component) in combination with the catalyst temperature. It is believed that the hydrogen gas stream affects the deposition of the carbonaceous species by preventing their formation or by reacting with and (partially) removing these carbonaceous deposits from this degraded catalyst, thereby extending catalyst lifetime. This "carbonaceous deposit removal rate" is primarily a function of the partial pressure of hydrogen at the active site of the catalyst in combination with the catalyst temperature. However, if the hydrogen partial pressure is too high at the active site of the catalyst, the oxygenate-to-hydrocarbon conversion is reduced leading to an inefficient process. Accordingly, the catalyst temperature, the partial pressure of hydrogen, and the partial pressure of oxygenate at the active site of the catalyst may be balanced to both increase the lifetime of the solid microporous acid component without significantly reducing the oxygenate-to-hydrocarbon conversion.

In processes according to the present embodiments, a hydrogen gas stream 101 is fed into the reaction zone 100. The hydrogen gas stream 101 is essentially a pure hydrogen gas stream comprising greater than or equal to 99.0 vol % $H_2$, such as greater than or equal to 99.5 vol % $H_2$, or even 100 vol % $H_2$. It should be understood that the hydrogen recycle stream 104, which is discussed in more detail below, will not have the same purity as the hydrogen gas stream 101. The hydrogen gas stream 101 may be introduced into the reaction zone 100 at any suitable flow rate relative to other gases introduced into the reaction zone 100 such that the hydrogen gas within the reaction zone 100 has the desired partial pressure. The partial pressure of the hydrogen gas within the reaction zone 100 is, in embodiments, from greater than or equal to 1 bar (100 kPa) to less than or equal to 48 bar (4800 kPa). In some embodiments, the partial pressure of the hydrogen in the reaction zone 100 is from greater than or equal to 1 bar (100 kPa) to less than or equal to 48 bar (4800 kPa), greater than or equal to 3 bar (300 kPa) to less than or equal to 48 bar (4800 kPa), greater than or equal to 8 bar (800 kPa) to less than or equal to 48 bar (4800 kPa), greater than or equal to 10 bar (1000 kPa) to less than or equal to 48 bar (4800 kPa), greater than or equal to 15 bar (1500 kPa) to less than or equal to 48 bar (4800 kPa), greater than or equal to 20 bar (2000 kPa) to less than or equal to 48 bar (4800 kPa), greater than or equal to 25 bar (2500 kPa) to less than or equal to 48 bar (4800 kPa), greater than or equal to 30 bar (3500 kPa) to less than or equal to 48 bar (4800 kPa), greater than or equal to 35 bar (3500 kPa) to less than or equal to 48 bar (4800 kPa), or greater than or equal to 40 bar (4000 kPa) to less than or equal to 48 bar (4800 kPa).

In yet other embodiments, the partial pressure of the hydrogen in the reaction zone 100 is from greater than or equal to 1 bar (100 kPa) to less than or equal to 45 bar (4500 kPa), greater than or equal to 1 bar (100 kPa) to less than or equal to 40 bar (4000 kPa), greater than or equal to 1 bar (100 kPa) to less than or equal to 35 bar (3000 kPa), greater than or equal to 1 bar (100 kPa) to less than or equal to 30 bar (3000 kPa), greater than or equal to 1 bar (100 kPa) to less than or equal to 25 bar (2500 kPa), greater than or equal to 1 bar (100 kPa) to less than or equal to 20 bar (2000 kPa), greater than or equal to 1 bar (100 kPa) to less than or equal to 15 bar (1500 kPa), greater than or equal to 1 bar (100 kPa) to less than or equal to 10 bar (1000 kPa), greater than or equal to 1 bar (100 kPa) to less than or equal to 8 bar (800 kPa), greater than or equal to 1 bar (100 kPa) to less than or equal to 6 bar (600 kPa), or greater than or equal to 1 bar (100 kPa) to less than or equal to 4 bar (400 kPa).

In processes according to embodiments, a feed gas stream 102 is fed into the reaction zone 100. The feed gas stream 102 comprises at least one oxygenate. In some embodiments, the oxygenate in the feed gas stream 102 is primarily methanol, dimethyl ether (DME), and mixtures thereof. However, in various embodiments, other oxygenates (besides methanol and DME) may be present in the feed gas stream 102 in low amounts, such as in amounts less than 0.5 wt %, less than 0.4 wt %, less than 0.3 wt %, less than 0.2 wt %, or less than 0.1 wt %, as impurities. These oxygenates include ethanol, n-propanol, isopropanol, methyl ethyl ether, dimethyl ether, diethyl ether, di-isopropyl ether, formaldehyde, dimethyl carbonate, dimethyl ketone, acetic acid and mixtures thereof. As an example of a feed stream comprising impurities, U.S. Federal Grade AA methanol specifies total impurities content of less than 0.15 wt %, such that the methanol content is greater than 99.85 wt % with ethanol content of less than 10 mg/kg, acetone content less than 20 mg/kg, total acetone and aldehyde content less than 30 mg/kg and total acid expressed as acetic acid of less than 30 mg/kg and water content less than 0.10 wt %. In additional embodiments, the feed gas stream 102 may include water that has been intentionally added to the feed gas steam 102 or that is a byproduct of methanol to DME conversion. Accordingly, in embodiments, the feed gas stream 102 may comprise greater than or equal to 0 wt % to less than or equal to 78 wt % water, greater than or equal to 5 wt % to less than or equal to 70 wt % water, greater than or equal to 10 wt % to less than or equal to 65 wt % water, greater than or equal to 15 wt % to less than or equal to 60 wt % water, greater than or equal to 20 wt % to less than or equal to 55 wt % water, greater than or equal to 25 wt % to less than or equal to 50 wt % water, greater than or equal to 30 wt % to less than or equal to 45 wt % water, or greater than or equal to 40 wt % to less than or equal to 45 wt % water.

The feed gas stream 102 may be introduced into the reaction zone 100 at any suitable flow rate relative to other gases introduced into the reaction zone 100 such that the oxygenate within the reaction zone 100 has the desired partial pressure. The partial pressure of the oxygenate within the reaction zone 100 is, in embodiments, from greater than or equal to 0.01 bar (1 kPa) to less than or equal to 7.00 bar (700 kPa). In some embodiments, the partial pressure of the hydrogen in the reaction zone 100 is from greater than or equal to 0.02 bar (2 kPa) to less than or equal to 7.00 bar (700 kPa), greater than or equal to 0.05 bar (5 kPa) to less than or equal to 7.00 bar (700 kPa), greater than or equal to 0.1 bar (10 kPa) to less than or equal to 7.00 bar (700 kPa), greater than or equal to 0.5 bar (50 kPa) to less than or equal to 7.00 bar (700 kPa), greater than or equal to 0.75 bar (75 kPa) to less than or equal to 7.00 bar (700 kPa), greater than or equal to 1.00 bar (100 kPa) to less than or equal to 7.00 bar (700 kPa), greater than or equal to 1.50 bar (150 kPa) to less than or equal to 7.00 bar (700 kPa), greater than or equal to 2.00 bar (200 kPa) to less than or equal to 7.00 bar (700 kPa), greater than or equal to 2.50 bar (250 kPa) to less than or equal to 7.00 bar (700 kPa), greater than or equal to 3.00 bar (300 kPa) to less than or equal to 7.00 bar (700 kPa), greater than or equal to 3.50 bar (350 kPa) to less than or equal to 7.00 bar (700 kPa), greater than or equal to 4.00 bar (400 kPa) to less than or equal to 7.00 bar (700 kPa), greater than or equal to 4.50 bar (450 kPa) to less than or equal to 7.00 bar (700 kPa), greater than or equal to 5.00 bar (500 kPa) to less than or equal to 7.00 bar (700 kPa), greater than or equal to 5.50 bar (550 kPa) to less than or equal to 7.00 bar (700 kPa), greater than or equal to 6.00 bar (600 kPa) to less than or equal to 7.00 bar (700 kPa), or greater than or equal to 6.50 bar (650 kPa) to less than or equal to 7.00 bar (700 kPa).

In yet other embodiments, the partial pressure of the oxygenate in the reaction zone 100 is from greater than or equal to 0.01 bar (1 kPa) to less than or equal to 6.50 bar (650 kPa), greater than or equal to 0.01 bar (1 kPa) to less than or equal to 6.00 bar (600 kPa), greater than or equal to 0.01 bar (1 kPa) to less than or equal to 5.50 bar (550 kPa), greater than or equal to 0.01 bar (1 kPa) to less than or equal to 5.00 bar (500 kPa), greater than or equal to 0.01 bar (1 kPa) to less than or equal to 4.50 bar (450 kPa), greater than or equal to 0.01 bar (1 kPa) to less than or equal to 4.00 bar (400 kPa), greater than or equal to 0.01 bar (1 kPa) to less than or equal to 3.50 bar (350 kPa), greater than or equal to 0.01 bar (1 kPa) to less than or equal to 3.00 bar (300 kPa), greater than or equal to 0.01 bar (1 kPa) to less than or equal to 2.50 bar (250 kPa), greater than or equal to 0.01 bar (1 kPa) to less than or equal to 2.00 bar (200 kPa), greater than or equal to 0.01 bar (1 kPa) to less than or equal to 1.50 bar (150 kPa), greater than or equal to 0.01 bar (1 kPa) to less than or equal to 1.00 bar (100 kPa), greater than or equal to 0.01 bar (1 kPa) to less than or equal to 0.75 bar (75 kPa), greater than or equal to 0.01 bar (1 kPa) to less than or equal to 0.50 bar (50 kPa), greater than or equal to 0.01 bar (1 kPa) to less than or equal to 0.10 bar (10 kPa), greater than or equal to 0.01 bar (1 kPa) to less than or equal to 0.05 bar (5 kPa), or greater than or equal to 0.01 bar (1 kPa) to less than or equal to 0.02 bar (2 kPa).

In still other embodiments, the partial pressure of the oxygenate in the reaction zone 100 is from greater than or equal to 0.01 bar (1 kPa) to less than or equal to 0.05 bar (5 kPa), greater than or equal to 0.02 bar (2 kPa) to less than or equal to 0.05 bar (5 kPa), greater than or equal to 0.03 bar (3 kPa) to less than or equal to 0.05 bar (5 kPa), or greater than or equal to 0.04 bar (4 kPa) to less than or equal to 0.05 bar (5 kPa).

In yet further embodiments, the partial pressure of the oxygenate in the reaction zone 100 is from greater than or equal to 0.10 bar (10 kPa) to less than or equal to 6.75 bar (675 kPa), greater than or equal to 0.50 bar (50 kPa) to less than or equal to 6.50 bar (650 kPa), greater than or equal to 1.00 bar (100 kPa) to less than or equal to 6.00 bar (600 kPa), greater than or equal to 1.50 bar (150 kPa) to less than or equal to 5.50 bar (550 kPa), greater than or equal to 2.00 bar (200 kPa) to less than or equal to 5.00 bar (500 kPa), greater than or equal to 2.50 bar (250 kPa) to less than or equal to 4.50 bar (450 kPa), or greater than or equal to 3.00 bar (300 kPa) to less than or equal to 4.00 bar (400 kPa).

In embodiments, the flow rate of the hydrogen gas stream 101 and the feed gas stream 102 may be modified to achieve the desired partial pressure of hydrogen and partial pressure of oxygenate in the reaction zone 100. In additional embodiments, the flow rate of the recycle stream 104 can also be used to modify the partial pressure of the hydrogen in the reaction zone 100. In still other embodiments, an inert gas stream (not shown in the FIGURE) may be introduced with the hydrogen gas stream 101 and the feed gas stream 102 to regulate the partial pressures of hydrogen and oxygenate in the reaction zone 100. In certain embodiments, the inert gas may be nitrogen, helium, or argon. It should be understood that the flow rate of any of the above streams can be used individually or in any combination to modify the partial pressure of the hydrogen in the reaction zone 100. The hydrogen should be present when the oxygenate reacts with the solid microporous acid component. Thus, in embodiments, the hydrogen gas stream 101 is introduced into the reaction zone 100 simultaneously with the feed gas stream 102. In other embodiments, the hydrogen gas stream 101 is introduced into the reaction zone 100 prior to the introduction of the feed gas stream 102 to pre-load the reaction zone 100 with hydrogen prior to the introduction of the feed gas stream 102.

The partial pressures of the hydrogen and oxygenate at the active site of the catalyst are not the only reaction conditions that affect the lifetime of the solid microporous acid component. The temperature of the catalyst also affects the lifetime of the solid microporous acid component. Thus, in embodiments, the partial pressure of the hydrogen in the reaction zone 100, the partial pressure of the oxygenate in the reaction zone 100, and the temperature of the reaction zone 100 are balanced to increase the lifetime of the solid microporous acid component while maintaining the efficiency of the oxygenate-to-hydrocarbon conversion.

In some embodiments, the temperature in the reaction zone 100 during the oxygenate-to-hydrocarbon conversion is from greater than or equal to 350° C. to less than or equal to 600° C., such as from greater than or equal to 350° C. to less than or equal to 500° C. In other embodiments, the temperature in the reaction zone 100 during the oxygenate-to-hydrocarbon conversion is from greater than or equal to 375° C. to less than or equal to 500° C., greater than or equal to 400° C. to less than or equal to 500° C., greater than or equal to 425° C. to less than or equal to 500° C., or greater than or equal to 425° C. to less than or equal to 475° C. In yet other embodiments, the temperature in the reaction zone 100 during the oxygenate-to-hydrocarbon conversion is from greater than or equal to 350° C. to less than or equal to 475° C., greater than or equal to 350° C. to less than or equal to 450° C., greater than or equal to 350° C. to less than or equal to 425° C., or greater than or equal to 375° C. to less than or equal to 425° C. In still other embodiments, the temperature in the reaction zone 100 during the oxygenate-to-hydrocarbon conversion is from greater than or equal to 375° C. to less than or equal to 425° C., or greater than or equal to 425° C. to less than or equal to 475° C.

Balancing the partial pressure of the hydrogen in the reaction zone 100, the partial pressure of the oxygenate in the reaction zone 100, and the temperature of the reaction zone 100 during the oxygenate-to-hydrocarbon conversion increases the lifetime of the solid microporous acid component. As defined herein, the "lifetime" of the microporous acid component is calculated as the cumulative amount of oxygenate converted to $C_2+C_3$ hydrocarbons per gram of the microporous acid component up to the point where the yield to $C_2+C_3$ hydrocarbons has dropped to zero. Including hydrogen at the active site of the catalyst increases the lifetime of the microporous acid component as compared to reaction zones where no hydrogen is added. The extent of the increase in the lifetime of the microporous acid component will vary as the partial pressure of the oxygenate, the partial pressure of the hydrogen, and the temperature are balanced. Although various embodiments described herein are defined as having a maximum lifetime of the microporous acid component, it should be understood that in some embodiments the partial pressure of the oxygenate at the active site of the catalyst, the partial pressure of hydrogen at the active site of the catalyst, and the temperature of the catalyst may be balanced such that the lifetime of the microporous acid component is essentially infinite.

In some embodiments where the catalyst comprises a microporous acid component having 8-MR access, the lifetime of the solid microporous acid component is greater than 15 g oxygenate converted/g solid microporous acid component, greater than or equal to 30 g oxygenate converted/g solid microporous acid component, greater than or equal to 50 g oxygenate converted/g solid microporous acid component, greater than or equal to 75 g oxygenate converted/g solid microporous acid component, greater than or equal to 100 g oxygenate converted/g solid microporous acid component, greater than or equal to 125 g oxygenate converted/g solid microporous acid component, greater than or equal to 150 g oxygenate converted/g solid microporous acid component, greater than or equal to 175 g oxygenate converted/g solid microporous acid component, greater than or equal to 200 g oxygenate converted/g solid microporous acid component, greater than or equal to 225 g oxygenate converted/g solid microporous acid component, greater than or equal to 250 g oxygenate converted/g solid microporous acid component, greater than or equal to 275 g oxygenate converted/g solid microporous acid component, greater than or equal to 300 g oxygenate converted/g solid microporous acid component, greater than or equal to 325 g oxygenate converted/g solid microporous acid component, greater than or equal to 350 g oxygenate converted/g solid microporous acid component, greater than or equal to 375 g oxygenate converted/g solid microporous acid component, greater than or equal to 400 g oxygenate converted/g solid microporous acid component, greater than or equal to 425 g oxygenate converted/g solid microporous acid component, or greater than or equal to 450 g oxygenate converted/g solid microporous acid component. In other embodiments, the lifetime of the solid microporous acid component is from greater than or equal to 6 to less than or equal to 450 g oxygenate converted/g solid microporous acid component, greater than or equal to 10 to less than or equal to 425 g oxygenate converted/g solid microporous acid component, greater than or equal to 25 to less than or equal to 400 g oxygenate converted/g solid microporous acid component, greater than or equal to 50 to less than or equal to 375 g oxygenate converted/g solid microporous acid component, greater than or equal to 75 to less than or equal to 350 g oxygenate converted/g solid microporous acid component, greater than or equal to 100 to less than or equal to 325 g oxygenate converted/g solid microporous acid component, greater than or equal to 125 to less than or equal to 300 g oxygenate converted/g solid microporous acid component, greater than or equal to 150 to less than or equal to 275 g oxygenate converted/g solid microporous acid component, greater than or equal to 175 to less than or equal to 250 g oxygenate converted/g solid microporous acid component, or greater than or equal to 200 to less than or equal to 225 g oxygenate converted/g solid microporous acid component.

In some embodiments where the catalyst comprises a microporous acid component having 10-MR access, the lifetime of the solid microporous acid component is greater than 150 g oxygenate converted/g solid microporous acid component, greater than 175 g oxygenate converted/g solid microporous acid component, greater than 200 g oxygenate converted/g solid microporous acid component, greater than 225 g oxygenate converted/g solid microporous acid component, greater than 250 g oxygenate converted/g solid microporous acid component, greater than or equal to 275 g oxygenate converted/g solid microporous acid component, greater than or equal to 300 g oxygenate converted/g solid microporous acid component, greater than or equal to 325 g oxygenate converted/g solid microporous acid component, greater than or equal to 350 g oxygenate converted/g solid microporous acid component, greater than or equal to 375 g oxygenate converted/g solid microporous acid component, greater than or equal to 400 g oxygenate converted/g solid microporous acid component, greater than or equal to 425 g oxygenate converted/g solid microporous acid component, greater than or equal to 450 g oxygenate converted/g solid microporous acid component, greater than or equal to 475 g oxygenate converted/g solid microporous acid component, greater than or equal to 500 g oxygenate converted/g solid microporous acid component, greater than or equal to 525 g oxygenate converted/g solid microporous acid component, greater than or equal to 550 g oxygenate converted/g solid microporous acid component, greater than or equal to 575 g oxygenate converted/g solid microporous acid component, greater than or equal to 600 g oxygenate converted/g solid microporous acid component, greater than or equal to 625 g oxygenate converted/g solid microporous acid component, or greater than or equal to 650 g oxygenate converted/g solid microporous acid component. In other embodiments, the lifetime of the solid microporous acid component is from greater than or equal to 6 to less than or equal to 625 g oxygenate converted/g solid microporous acid component, greater than or equal to 10 to less than or equal to 600 g oxygenate converted/g solid microporous acid component, greater than or equal to 25 to less than or equal to 550 g oxygenate converted/g solid microporous acid component, greater than or equal to 50 to less than or equal to 500 g oxygenate converted/g solid microporous acid component, greater than or equal to 75 to less than or equal to 450 g oxygenate converted/g solid microporous acid component, greater than or equal to 100 to less than or equal to 400 g oxygenate converted/g solid microporous acid component, greater than or equal to 125 to less than or equal to 350 g oxygenate converted/g solid microporous acid component, greater than or equal to 150 to less than or equal to 325 g oxygenate converted/g solid microporous acid component, greater than or equal to 175 to less than or equal to 300 g oxygenate converted/g solid microporous acid component, greater than or equal to 200 to less than or equal to 275 g oxygenate converted/g solid microporous acid component, or greater than or equal to 225 to less than or equal to 250 g oxygenate converted/g solid microporous acid component.

Although the lifetime of the solid microporous acid component can be increased by increasing the partial pressure of hydrogen in the reaction zone 100, increasing the partial pressure of hydrogen in the reaction zone 100 too much will affect the oxygenate-to-hydrocarbon conversion in a negative way. However, by balancing the partial pressure of the hydrogen, the partial pressure of the oxygenates, and the temperature, the composition of the product stream may be controlled. For instance, the ratio of olefins to paraffins in the product stream may be controlled. In embodiments, average ratio of olefins to paraffins in the product stream 103 is greater than or equal to 0.01. As referred to herein, the olefin to paraffin ratio is expressed as the volume of olefins to the volume of paraffins in the product stream. In some embodiments, the average ratio of olefins to paraffins in the product stream 103 is greater than or equal to 0.05, greater than or equal to 0.10, greater than or equal to 0.50, greater than or equal to 1.00, greater than or equal to 1.50, or greater than or equal to 2.00. In still other embodiments, the average ratio of olefins to paraffins in the product stream 103 is greater than or equal to 7.00, greater than or equal to 8.00, or greater than or equal to 9.00. In some embodiments, the partial pressure hydrogen, the partial pressure of the oxygenate, and the temperature may be balanced such that the ratio of olefins to paraffins approaches infinity (i.e., where the amount of paraffins is essentially 0).

Likewise, in embodiments, balancing the partial pressure of the oxygenate, the partial pressure of the hydrogen, and the temperature allows for one to control the volume of $C_2$ to the volume of $C_3$. As referred to herein, the $C_2$ to $C_3$ ratio is expressed as the volume of $C_2$ products to the volume of $C_3$ products in the product stream. In embodiments, the $C_2$ to $C_3$ product ratio in the product stream 103 is from greater than or equal to 0.1 to less than or equal to 2.7. In some embodiments, the $C_2$ to $C_3$ product ratio in the product stream 103 is from greater than or equal to 0.4 to less than or equal to 2.6, greater than or equal to 0.6 to less than or equal to 2.5, greater than or equal to 0.8 to less than or equal to 2.4, greater than or equal to 1.0 to less than or equal to 2.2, greater than or equal to 1.2 to less than or equal to 2.0, or greater than or equal to 1.4 to less than or equal to 1.8.

Once the product stream exits the reaction zone 100, it may, in some embodiments, be introduced into a separator 120 that separates hydrogen components, which may include methane, in the product stream 103 from the hydrocarbon products. The hydrogen components from the product stream 103 can then be sent to the reaction zone 100 via a hydrogen recycle stream 104. It should be understood that, although not depicted in the FIGURE, the hydrogen recycle stream may be introduced to treatment equipment that converts the hydrogen component to pure hydrogen.

A final product stream 105 also exits the separator 120. The final product stream contains desired hydrocarbon products, such as, for example, $C_2$ to $C_5$ olefins and paraffins. It should be understood that the final product stream 105 may be introduced to any suitable separation equipment that separates the desired products from undesired constituents in the final product stream 105, or that separates desired products in the final product stream 105 from one another.

In various embodiments, any of the partial pressures of the hydrogen in the reaction zone, the partial pressures of the oxygenate in the reaction zone, and the temperatures of the reaction zone during the oxygenate-to-hydrocarbon conversion disclosed above may individually be selected and combined with any other individually disclosed partial pressure of the hydrogen, partial pressure of the oxygenate, and temperature of the reaction zone. Embodiments disclosed herein envision and include any variation of the above-disclosed process conditions.

In a particular embodiment, the partial pressure of the hydrogen in the reaction zone is from greater than or equal to 1 bar (100 kPa) to less than or equal to 40 bar (4000 kPa), such as from greater than or equal to 2 bar (200 kPa) to less than or equal to 35 bar (3500 kPa), the partial pressure of the oxygenate in the reaction zone is from greater than or equal to greater than or equal to 0.01 bar (1 kPa) to less than or equal to 0.05 bar (5 kPa), such as from greater than or equal to 0.01 bar (1 kPa) to less than or equal to 0.02 bar (2 kPa), and the temperature of the reaction zone during the oxygenate-to-hydrocarbon conversion is from greater than or equal to 375° C. to less than or equal to 425° C., such as about 400° C. In this embodiment, the lifetime of the solid microporous acid component is from greater than or equal to 6 to less than or equal to 450 g oxygenate/g solid microporous acid component. Further, the average olefin to paraffin ratio of a product stream produced by this embodiment is greater than or equal to 1, such as greater than or equal to 3. The $C_2$ to $C_3$ ratio of a product stream produced by this embodiment is from greater than or equal to 0.5 to less than or equal to 1.2, such as from greater than or equal to 0.6 to less than or equal to 1.0.

In another particular embodiment, the partial pressure of the hydrogen in the reaction zone is from greater than or equal to 1 bar (100 kPa) to less than or equal to 48 bar (4800 kPa), such as from greater than or equal to 5 bar (500 kPa) to less than or equal to 40 bar (4000 kPa), the partial pressure of the oxygenate in the reaction zone is from greater than or equal to greater than or equal to 0.1 bar (10 kPa) to less than or equal to 6.75 bar (675 kPa), such as from greater than or equal to 0.5 bar (50 kPa) to less than or equal to 6.50 bar (650 kPa), and the temperature of the reaction zone during the oxygenate-to-hydrocarbon conversion is from greater than or equal to 425° C. to less than or equal to 475° C., such as about 450° C. In this embodiment, the lifetime of the solid microporous acid component is from greater than or equal to 6 to less than or equal to 225 g oxygenate/g solid microporous acid component. Further, the average olefin to paraffin ratio of a product stream produced by this embodiment is greater than or equal to 0.01, such as greater than or equal to 0.05. The $C_2$ to $C_3$ ratio of a product stream produced by this embodiment is from greater than or equal to 0.2 to less than or equal to 1.5.

EXAMPLES

Embodiments will be further clarified by the following examples.

Example 1

In Example 1, processes are compared where the oxygenate, which is methanol in Example 1, partial pressure is maintained at conventional levels and the hydrogen partial pressure is varied to show the effect that the hydrogen partial pressure has on the lifetime of the solid microporous acid, which in the samples of Example 1 is SAPO-34. Example 1 shows that the partial pressure of hydrogen has a large effect on the lifetime of the solid microporous acid.

A component of the solid microporous acid (i.e., SAPO-34) was formed by stirring together 8.2 grams of aluminum isopropoxide ($Al(OC_3H_7)_3$) with a solution of 3.9 grams of 85 wt % orthophosphoric acid in 8.4 grams of water. Subsequently, 1.2 grams of an aqueous sol of 30 wt % $SiO_2$ (Ludox AS-30) and 0.5 grams of water were stirred into the mixture until the resultant was homogeneous. Finally, 16.8 grams of an aqueous solution of 35 wt % tetraethylammonium hydroxide (TEAOH) was added to the mixture to form the reaction mixture.

Once formulated, the reaction mixture was placed in a stainless steel stirred Parr reactor and heated to 200° C. at 0.5° C./min. The temperature was maintained for 120 hours under autogenous pressure while stirring at 60 RPM. The product was recovered by centrifugation, washed with water and dried at 90° C. overnight.

A portion of the recovered product required for catalytic testing was calcined in a muffle furnace in air to remove the templating agent. This was accomplished by gradually increasing the temperature in the furnace to 600° C. at a heating rate of 2° C./min, and holding at 600° C. for a period of 4 hours. This calcined material was used in the subsequent samples and examples as the SAPO-34 component.

Once the SAPO-34 was produced as disclosed above, 2.4 mg of the above-formulated SAPO-34 was mixed with 2.5 g Silicon Carbide (SiC) and this mixture was loaded into a reactor.

The process for each of the samples in Example 1 begins as follows. A flow of 10 sccm nitrogen was applied over the reactor bed. The reactor pressure was set to 50 bar (5000 KPa) and the reactor temperature was set to the value as indicated below for each of the individual samples. Once the temperature and pressure setpoints had been reached, the feed flow as indicated below was applied and the reactor outlet composition was measured.

The feed streams for each of the samples in Example 1 are: Feed A1 was a mixture of 710 vol (ppm) Methanol/10 vol % Nitrogen/90 vol % Helium; Feed A2 was a mixture of 1065 vol (ppm) Methanol/10 vol % Nitrogen/90 vol % Helium; Feed B was 100 vol % Helium; and feed C was 100 vol % Hydrogen.

Sample CE1

The first sample (CE1) of Example 1 is a comparative example where hydrogen is not added to the reaction zone during the process. Sample CE1 was conducted at 400° C. using the following feeds and flow rates: Feed A1 at 100 sccm; and Feed B at 200 sccm. The measured results for CE1 are shown in Table 1 below.

Sample E1

The second through sixth samples (E1-E5) show the effect that hydrogen partial pressure has on the lifetime of the SAPO-34. Sample E1 was conducted at 400° C. using the following feeds and flow rates: Feed A2 at 100 sccm; Feed B at 180 sccm; and Feed C at 6 sccm. The measured results for E1 are shown in Table 1 below.

Sample E2

Sample E2 was conducted at 400° C. using the following feeds and flow rates: Feed A1 at 100 sccm; Feed B at 180 sccm; and Feed C at 20 sccm. The measured results for E2 are shown in Table 1 below.

Sample E3

Sample E3 was conducted at 400° C. using the following feeds and flow rates: Feed A1 at 100 sccm; Feed B at 150 sccm; and Feed C at 50 sccm. The measured results for E3 are shown in Table 1 below.

Sample E4

Sample E3 was conducted at 400° C. using the following feeds and flow rates: Feed A1 at 100 sccm; and Feed C at 200 sccm. The measured results for E4 are shown in Table 1 below.

Sample E5

Sample E5 was conducted at 400° C. using the following feeds and flow rates: Feed A2 at 50 sccm; and Feed C at 200 sccm. The measured results for E5 are shown in Table 1 below.

Sample E6

The seventh and eighth samples (E6 and E7) show the effect that temperature has on the lifetime of the SAPO-34. Sample E6 was conducted at 350° C. using the following feeds and flow rates: Feed A2 at 100 sccm; Feed B at 150 sccm; and Feed C at 50 sccm. The measured results for E6 are shown in Table 1 below.

Sample E7

Sample E7 was conducted at 500° C. using the following feeds and flow rates: Feed A2 at 100 sccm; Feed B at 150 sccm; and Feed C at 50 sccm. The measured results for E7 are shown in Table 1 below.

Example 2

In Example 2, processes are compared where the oxygenate, which is methanol in Example 2, partial pressure and the hydrogen partial pressure are varied to show the effect that each partial pressure has on the lifetime of the solid microporous acid, which in the samples of Example 2 are SAPO-34. Example 2 shows that the partial pressure of the oxygenate and the partial pressure of hydrogen have a large effect on the lifetime of the solid microporous acid and can be balanced to yield a process that provides a desired product while at the same time increasing the lifetime of the solid microporous acid.

Once the SAPO-34 was produced as disclosed in Example 1 above, 500 mg of SAPO-34 was loaded into a reactor.

The process for each of the samples in Example 2 begins as follows. A flow of 10 sccm nitrogen was applied over the reactor bed. The reactor pressure and the reactor temperature were set to the value as indicated below for each of the individual samples. Once the temperature and pressure setpoints had been reached, the feed flow as indicated below was applied and the reactor outlet composition was measured.

The feed streams for each of the samples in Example 2 are: Feed A was a liquid stream of pure methanol (the liquid is evaporated in a pre-heater before it enters the reactor as a gas; Feed B was 100 vol % Nitrogen; and Feed C was 100 vol % Hydrogen.

Sample CE2

The first sample (CE2) of Example 2 is a comparative example where hydrogen is not added to the reaction zone during the process. Sample CE2 was conducted at 450° C. and 1 bar (100 kPa) using the following feeds and flow rates: Feed A at 0.01 ml liquid/min; and Feed B at 55 sccm. The measured results for CE2 are shown in Table 2 below.

Sample E8

Sample E8 was conducted at 450° C. and 1 bar (100 kPa) using the following feeds and flow rates: Feed A at 0.01 ml liquid/min; Feed B at 10 sccm; and Feed C at 45 sccm. The measured results for E8 are shown in Table 2 below.

Sample E9

Sample E9 was conducted at 450° C. and 20 bar (2000 kPa) using the following feeds and flow rates: Feed A at 0.01 ml liquid/min; Feed B at 10 sccm; and Feed C at 45 sccm. The measured results for E9 are shown in Table 2 below.

Sample E10

Sample E10 was conducted at 450° C. and 30 bar (3000 kPa) using the following feeds and flow rates: Feed A at 0.01 ml liquid/min; Feed B at 10 sccm; and Feed C at 45 sccm. The measured results for E10 are shown in Table 2 below.

TABLE 1

| Sample | Hydrogen partial pressure [bar] | Methanol partial pressure [bar] | Temperature [deg C] | Lifetime: cumulative amount of MeOH converted to $C_2 + C_3$ hydrocarbons [gram MeOH/gram SAPO-34] | Average Olefin/ Paraffin ratio [v/v] | $C_2/C_3$ product ratio at t = 0 hrs [v/v] |
|---|---|---|---|---|---|---|
| CE1 | 0 | 0.01 | 400 | 2 | Infinite | 1.5 |
| E1 | 1 | 0.02 | 400 | 6 | Infinite | 1.2 |
| E2 | 3 | 0.01 | 400 | 28 | 12 | 1.2 |
| E3 | 8 | 0.01 | 400 | 450 | 7 | 1.2 |
| E4 | 33 | 0.01 | 400 | 166 | 1 | 0.6 |
| E5 | 40 | 0.01 | 400 | 28 | 1 | 0.6 |
| E6 | 8 | 0.02 | 350 | 1 | Infinite | 1.0 |
| E7 | 8 | 0.02 | 500 | 1 | 3 | 2.2 |

Sample E11

Sample E11 was conducted at 450° C. and 50 bar (5000 kPa) using the following feeds and flow rates: Feed A at 0.01 ml liquid/min; Feed B at 10 sccm; and Feed C at 45 sccm. The measured results for E11 are shown in Table 2 below.

Sample E12

Sample E12 was conducted at 450° C. and 65 bar (6500 kPa) using the following feeds and flow rates: Feed A at 0.01 ml liquid/min; Feed B at 10 sccm; and Feed C at 45 sccm. The measured results for E12 are shown in Table 2 below.

Sample E13

Sample E13 was conducted at 350° C. and 50 bar (5000 kPa) using the following feeds and flow rates: Feed A at 0.01 ml liquid/min; Feed B at 10 sccm; and Feed C at 45 sccm. The measured results for E13 are shown in Table 2 below.

Sample E14

Sample E14 was conducted at 500° C. and 50 bar (5000 kPa) using the following feeds and flow rates: Feed A at 0.01 ml liquid/min; Feed B at 10 sccm; and Feed C at 45 sccm. The measured results for E14 are shown in Table 2 below.

TABLE 2

| Sample | Hydrogen partial pressure [bar] | Methanol partial pressure [bar] | Temperature [deg C] | Lifetime: cumulative amount of MeOH converted to $C_2 + C_3$ hydrocarbons [gram MeOH/gram SAPO-34] | Average Olefin/ Paraffin ratio [v/v] | $C_2/C_3$ product ratio at t = 0 hrs [v/v] |
|---|---|---|---|---|---|---|
| CE2 | 0 | 0.10 | 450 | 6 | 22 | 1.5 |
| E8 | 1 | 0.10 | 450 | 6 | 22 | 1.5 |
| E9 | 15 | 2.01 | 450 | 37 | 2 | 0.3 |
| E10 | 22 | 3.01 | 450 | 77 | 0.8 | 0.3 |
| E11 | 37 | 5.02 | 450 | 223 | 0.02 | 0.2 |
| E12 | 48 | 6.52 | 450 | 123 | 0.01 | 0.2 |
| E13 | 37 | 5.02 | 350 | 21 | 0.07 | 2.7 |
| E14 | 37 | 5.02 | 500 | 49 | 0.07 | 0.1 |

Example 3

Example 3 shows the effect that hydrogen partial pressure and oxygenate, which in Example 3 is methanol, partial pressure have on the lifetime of a solid microporous acid, which in Example 3 is ZSM-5. Example 3 shows that the partial pressure of the oxygenate and the partial pressure of hydrogen have a large effect on the lifetime of the ZSM-5 solid microporous acid.

95 mg of a ZSM-5 catalyst (commercially available as Zeolyst CBV28014) was mixed with 1.5 gram Silicon Carbide (SiC). This mixture was then loaded into a reactor.

The process for each of the samples in Example 3 begins as follows. A flow of 10 sccm nitrogen was applied over the reactor bed. The reactor temperature was set to 450° C. and the reactor pressure was set to the value as indicated below for each of the individual samples. Once the temperature and pressure setpoints had been reached, the feed flow as indicated below was applied and the reactor outlet composition was measured.

The feed streams for each of the samples in Example 3 are: Feed A was a liquid stream of pure methanol (the liquid is evaporated in a pre-heater before it enters the reactor as a gas; Feed B was 100 vol % Nitrogen; and Feed C was 100 vol % Hydrogen.

Sample CE3

The first sample (CE3) of Example 3 is a comparative example where hydrogen is not added to the reaction zone during the process. Sample CE3 was conducted at 1 bar (100 kPa) using the following feeds and flow rates: Feed A at 0.04 ml liquid/min; and Feed B at 200 sccm. The measured results for CE3 are shown in Table 3 below.

Sample E15

Sample E15 was conducted at 10 bar (1000 kPa) using the following feeds and flow rates: Feed A at 0.04 ml liquid/min; Feed B at 22 sccm; and Feed C at 178 sccm. The measured results for E15 are shown in Table 3 below.

TABLE 3

| Sample | Hydrogen partial pressure [bar] | Methanol partial pressure [bar] | Temperature [deg C] | Lifetime: cumulative amount of MeOH converted to $C_2 + C_3$ hydrocarbons [gram MeOH/gram ZSM-5] | Average Olefin/ Paraffin ratio [v/v] | $C_2/C_3$ product ratio at t = 0 hrs [v/v] |
|---|---|---|---|---|---|---|
| CE3 | 0 | 0.11 | 450 | 73 | 13 | 0.3 |
| E15 | 8 | 1.09 | 450 | 622 | 6 | 0.5 |

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for converting oxygenates to hydrocarbons, comprising:
   introducing a feed stream comprising at least one oxygenate into a reaction zone;
   introducing a hydrogen gas stream into the reaction zone;
   contacting the feed stream and the hydrogen gas stream simultaneously with a catalyst in the reaction zone, wherein the catalyst comprises a solid microporous acid component having 8-MR to 10-MR access, wherein the hydrogen gas stream in the reaction zone has a partial pressure from greater than or equal to 1 bar (100 kPa) to less than or equal to 48 bar (4800 kPa), and the reaction zone is at a temperature from greater than or equal to 350° C. to less than or equal to 500° C.

2. The process for converting oxygenates to hydrocarbons of claim 1, wherein the partial pressure of the at least one oxygenate in the reaction zone is from greater than or equal to 0.01 bar (1 kPa) to less than or equal to 7.00 bar (700 kPa).

3. The process for converting oxygenates to hydrocarbons of claim 1, wherein the solid microporous acid component is a molecular sieve having 8-MR access.

4. The process for converting oxygenates to hydrocarbons of claim 1, wherein the at least one oxygenate is selected from the group consisting of methanol, dimethyl ether, and mixtures thereof.

5. The process for converting oxygenates to hydrocarbons of claim 1, wherein the reaction zone is at a temperature from greater than or equal to 400° C. to less than or equal to 450° C.

6. The process for converting oxygenates to hydrocarbons of claim 1, wherein the solid microporous acid component meets one of the following criteria:
the solid microporous acid component has 8-MR access and a lifetime of the solid microporous acid component is greater than 15 g oxygenate converted/g solid microporous acid component; or
the solid microporous acid component has 10-MR access and a lifetime of the solid microporous acid component is greater than 150 g oxygenate converted/g solid microporous acid component, and
wherein the lifetime of the solid microporous acid component is defined as a cumulative amount of oxygenate converted to $C_2+C_3$ hydrocarbons per gram of microporous acid component up to a point where a conversion of the oxygenates to $C_2+C_3$ hydrocarbons has dropped to zero.

7. The process for converting oxygenates to hydrocarbons of claim 1, wherein an average volume ratio of olefins to paraffins in a product stream is from greater than or equal to 0.01.

8. The process for converting oxygenates to hydrocarbons of claim 1, wherein a $C_2$ to $C_3$ product volume ratio in a product stream is from greater than or equal to 0.1 to less than or equal to 2.7.

9. The process for converting oxygenates to hydrocarbons of claim 1, wherein an inert gas stream is introduced into the reaction zone.

10. A process for converting oxygenates to hydrocarbons, comprising:
introducing a feed stream comprising at least one oxygenate into a reaction zone;
introducing a hydrogen gas stream into the reaction zone;
contacting the feed stream and the hydrogen gas stream simultaneously with a catalyst in the reaction zone, wherein the catalyst comprises a solid microporous acid component having 8-MR to 10-MR access,
wherein the hydrogen gas stream in the reaction zone has a partial pressure from greater than or equal to 1 bar (100 kPa) to less than or equal to 40 bar (4000 kPa),
wherein the at least one oxygenate in the reaction zone has a partial pressure from greater than or equal to 0.01 bar (1 kPa) to less than or equal to 0.05 bar (5 kPa), and the reaction zone is at a temperature from greater than or equal to 375° C. to less than or equal to 425° C.

11. The process for converting oxygenates to hydrocarbons of claim 10, wherein the solid microporous acid component meets one of the following criteria:
the solid microporous acid component has 8-MR access and a lifetime of the solid microporous acid component is greater than 15 g oxygenate converted/g solid microporous acid component; or
the solid microporous acid component has 10-MR access and a lifetime of the solid microporous acid component is greater than 150 g oxygenate converted/g solid microporous acid component, and
wherein the lifetime of the solid microporous acid component is defined as a cumulative amount of oxygenate converted to $C_2+C_3$ hydrocarbons per gram of microporous acid component up to a point where a conversion of the oxygenates to $C_2+C_3$ hydrocarbons has dropped to zero.

12. The process for converting oxygenates to hydrocarbons of claim 10, wherein an average volume ratio of olefins to paraffins in a product stream is from greater than or equal to 1, and
wherein a $C_2$ to $C_3$ product volume ratio in a product stream is from greater than or equal to 0.5 to less than or equal to 1.2.

13. A process for converting oxygenates to hydrocarbons, comprising:
introducing a feed stream comprising at least one oxygenate into a reaction zone;
introducing a hydrogen gas stream into the reaction zone; contacting the feed stream and the hydrogen gas stream simultaneously with a catalyst in the reaction zone, wherein the catalyst comprises a solid microporous acid component having 8-MR to 10-MR access,
wherein the hydrogen gas stream in the reaction zone has a partial pressure from greater than or equal to 1 bar (100 kPa) to less than or equal to 48 bar (4800 kPa),
wherein the at least one oxygenate in the reaction zone has a partial pressure from greater than or equal to 0.1 bar (10 kPa) to less than or equal to 6.75 bar (675 kPa), and the reaction zone is at a temperature from greater than or equal to 425° C. to less than or equal to 475° C.

14. The process for converting oxygenates to hydrocarbons of claim 13, wherein the solid microporous acid component meets one of the following criteria:
the solid microporous acid component has 8-MR access and a lifetime of the solid microporous acid component is greater than 15 g oxygenate converted/g solid microporous acid component; or
the solid microporous acid component has 10-MR access and a lifetime of the solid microporous acid component is greater than 150 g oxygenate converted/g solid microporous acid component, and
wherein the lifetime of the solid microporous acid component is defined as a cumulative amount of oxygenate converted to $C_2+C_3$ hydrocarbons per gram of microporous acid component up to a point where a conversion of the oxygenates to $C_2+C_3$ hydrocarbons has dropped to zero.

15. The process for converting oxygenates to hydrocarbons of claim 13, wherein an average volume ratio of olefins to paraffins in a product stream is from greater than or equal to 0.01 to less than or equal to 22, and
wherein a $C_2$ to $C_3$ product volume ratio in a product stream is from greater than or equal to 0.2 to less than or equal to 1.5.

* * * * *